United States Patent [19]

Sumitomo et al.

[11] 4,422,085
[45] Dec. 20, 1983

[54] INK LIQUID VISCOSITY CONTROL IN AN INK LIQUID SUPPLY SYSTEM FOR AN INK JET SYSTEM PRINTER

[75] Inventors: Yuji Sumitomo, Yamatokoriyama; Yoshio Kanayama, Nabari, both of Japan

[73] Assignee: Sharp Kabushiki Kaisha, Osaka, Japan

[21] Appl. No.: 247,052

[22] Filed: Mar. 24, 1981

[30] Foreign Application Priority Data

Mar. 28, 1980 [JP] Japan ................................. 55-41762

[51] Int. Cl.³ ........................ G01D 15/16; G01N 9/18
[52] U.S. Cl. ................................. 346/140 R; 346/75; 137/91; 137/93; 73/453
[58] Field of Search ............... 346/140 R, 75; 137/92, 137/91, 93; 73/453

[56] References Cited

U.S. PATENT DOCUMENTS

| | | | |
|---|---|---|---|
| 3,952,761 | 4/1976 | Friedland | 73/445 X |
| 4,055,708 | 10/1977 | Yamamoto | 73/453 X |
| 4,130,126 | 12/1978 | Chocholaty et al. | 137/91 X |
| 4,270,133 | 5/1981 | Shimazawa et al. | 346/140 |

Primary Examiner—Stafford D. Schreyer
Attorney, Agent, or Firm—Birch, Stewart, Kolasch & Birch

[57] ABSTRACT

An ink liquid supply system for an ink jet system printer includes a sub tank for introducing a new ink liquid from an ink liquid cartridge and an old ink liquid from a beam gutter included in the ink jet system printer. A float element is disposed in the sub tank, the float element having a specific gravity of, for example, 1.062 which is slightly greater than the specific gravity of a preferred ink liquid suited for the ink jet system printer. In the normal operation mode, the float element is positioned at the bottom of the sub tank. When the ink liquid viscosity increases, the float element moves upward. A detection unit is associated with the float element to develop a control signal when the float element moves upward. In response to the control signal, a dilution is added to the ink liquid contained in the sub tank in order to reduce the viscosity of the ink liquid.

8 Claims, 4 Drawing Figures

INK LIQUID VISCOSITY CONTROL IN AN INK LIQUID SUPPLY SYSTEM FOR AN INK JET SYSTEM PRINTER

BACKGROUND AND SUMMARY OF THE INVENTION

The present invention relates to an ink liquid supply system for an ink jet system printer and, more particularly, to an ink liquid viscosity control system for maintaining the ink liquid viscosity within a preselected range.

An ink jet system printer of the charge amplitude controlling type has been widely used in, for example, a word processor, a facsimile printer and a computer output device. The ink jet system printer of the charge amplitude controlling type ensures a clean printing in a rapid and quiet operation.

In such an ink jet system printer, an ink liquid of a predetermined pressure is supplied to a nozzle to emit ink droplets at a preselected frequency. Ink droplets not contributing to the actual printing operation are directed to a beam gutter for recirculation purposes. Therefore, the ink liquid viscosity gradually increases while the printer operates because the volatile component included in the ink liquid volatilizes during time period when the ink droplets travel from the nozzle to the beam gutter through the air. On the other hand, it is strictly required that the ink liquid viscosity be maintained within a preselected range to ensure an accurate droplet formation.

A viscosity detection system is required if the system is desired to be constructed to control the ink liquid viscosity. Conventional viscosity detection systems of the laboratory type such as a rotation viscosimeter and an ultrasonic viscosimeter are expensive and occupy a large space. Thus, the conventional viscosity detection systems are not suited for detecting the ink liquid viscosity in an ink liquid supply system for an ink jet system printer. Further, the above-mentioned conventional viscosity detection systems must be placed in a constant temperature environment.

On the other hand, an ink liquid viscosity control system in an ink liquid supply system is disclosed in U.S. Pat. No. 4,190,846, INK LIQUID CONCENTRATION CONTROL IN AN INK LIQUID SUPPLY SYSTEM FOR AN INK JET SYSTEM PRINTER, issued on Feb. 26, 1980. In this system, a semipermeable membrane is employed to control the ink liquid concentration. Such a control system can not ensure a long period of operation due to the semipermeable membrane.

Accordingly, an object of the present invention is to provide an ink liquid viscosity control system in an ink liquid supply system for an ink jet system printer.

Another object of the present invention is to provide an ink liquid supply system for an ink jet system printer, which ensures an accurate operation of the printer.

Still another object of the present invention is to provide a small size ink liquid viscosity control device which ensures an accurate viscosity control.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

To achieve the above objects, pursuant to an embodiment of the present invention, an ink liquid viscosity detection unit is incorporated in a sub tank included in the ink liquid supply system for an ink jet system printer. The ink liquid viscosity detection unit includes a float element disposed in the ink liquid contained in the sub tank, the float element has a specific gravity slightly greater than the spcific gravity of an ink liquid of a preferred viscosity. When the ink liquid viscosity becomes large and the specific gravity of the ink liquid becomes greater than that of the float element, the float element moves upward. The upward movement of the float element is detected by a detection unit which develops a control signal to add a dilution to the ink liquid contained in the sub tank, thereby maintaining the ink liquid viscosity within a predetermined range.

BRIEF DESCRIPTION OF THE DRAWINGS

The present invention will be better understood from the detailed description given hereinbelow and the accompanying drawings which are given by way of illustration only, and thus are not limitative of the present invention and wherein.

DESCRIPTION OF THE PREFERRED EMBODIMENTS

In order to facilitate a complete understanding of the present invention ink liquid characteristics of the ink liquid used in the ink jet system printer will be first described with reference to FIG. 1.

The ink liquid includes a dye functioning as a coloring agent to provide a visible printout. The dye and a solvent are deposited on a recording paper to provide an image of which reflection optical density is between 0.8 and 1.3. The color is preferably real black.

The ink liquid is emitted from a nozzle toward a recording paper through an orifice of around 60 $\mu\phi$Therefore, the ink liquid must not be dried at the orifice. To prevent the blocking of the orifice portion, a moisten and solution promoting agent, for example, polyatomic glycol is added to the ink liquid.

Further, an antibacterial substance is added to the ink liquid for protecting the ink liquid from mold and bacteria. In addition to that, a chelate agent is added to the ink liquid for preventing the occurrence of precipitation caused by a chemical reaction occurring in the ink liquid which contacts the ink liquid supply devices.

In order to ensure a stable droplet formation and an accurate charging operation in an ink jet system printer of the charge amplitude controlling type, the coefficient of viscosity of the ink liquid must be held below 3 (three) cps (centipoise) and the electrical conductivity of the ink liquid must be held between 3 (three) and 7 (seven) ms/cm (millisiemens/centimeter). Further, the ink liquid must be safe if it accidentally comes in contact with the human body.

A preferred ink liquid which satisfies the above-mentioned various requirements is a water dilution ink liquid. That is, the preferred ink liquid includes a water as a solvent and includes a solute comprising the water dilution dye and various additive agents. The following TABLE I represents compositions of a preferred ink liquid used in an ink jet system printer.

TABLE I water dilution ink liquid
- volatile component ----- water (solvent)
- non-volatile component- (solute)
  - dye
  - moisten and solution promoting agent
  - antibacterial substance
  - chelate agent
  - buffer agent
  - infrared absorbing agent
  - (special additive)

The ink liquid used in the ink jet system printer is a dispersive liquid, wherein various solute components operate independently and never react with each other. A typical ink liquid used in the ink jet system printer includes a solute with a 22–32 weight percent, which has the coefficient of viscosity of 2.2–2.8 cps (centipoise) at room temperature (20° C.). It is not possible to eliminate the evaporation of the volatile component and, therefore, the coefficient of viscosity of the ink liquid becomes higher as a period of time passes when the volatile component is not added to the ink liquid.

Figure 1:
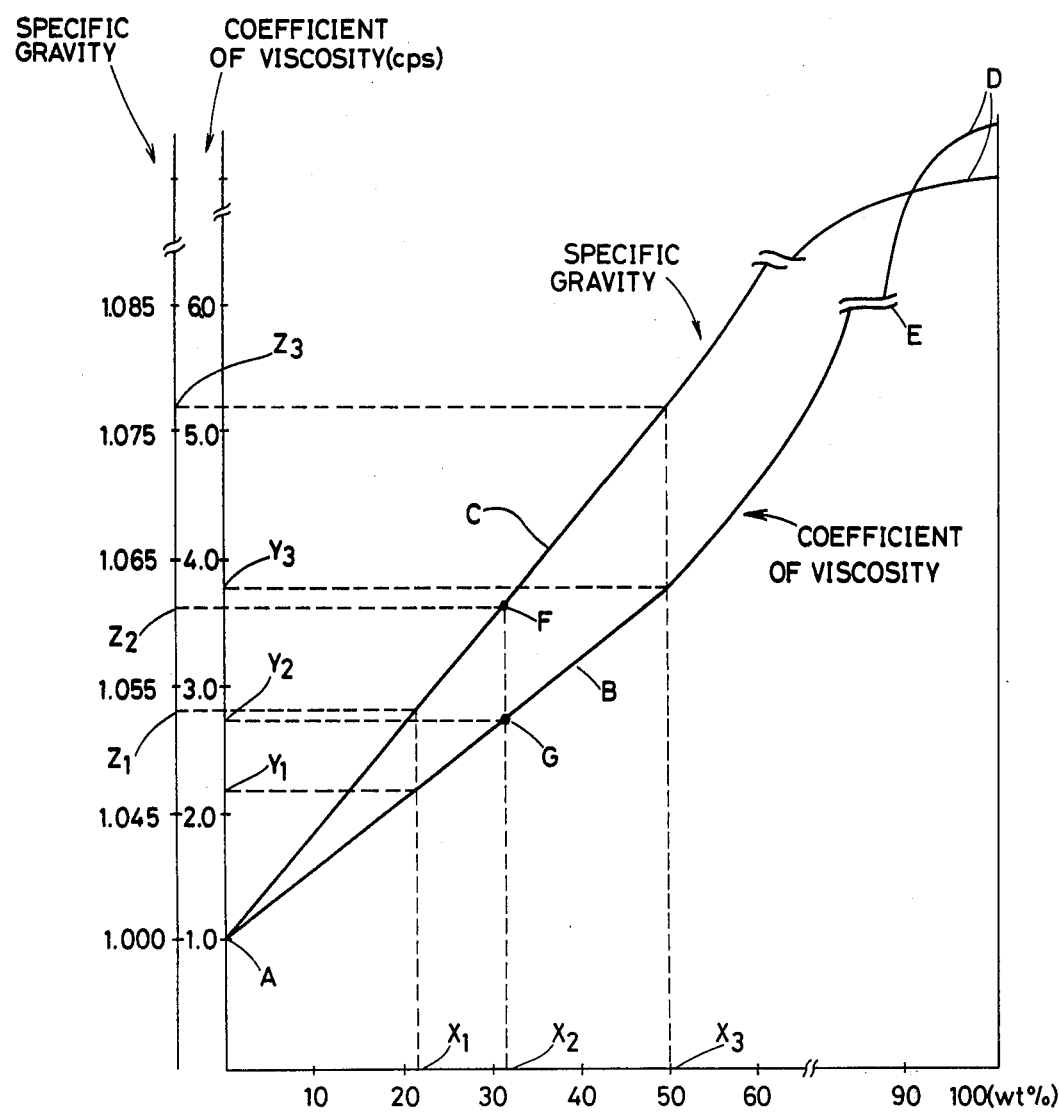
FIG. 1 is a graph showing the characteristics of an ink liquid used in an ink jet system printer.

FIG. 1 shows the relationships, at room temperature, between the weight percent of the solute (along the abscissa axis) and the specific gravity and the coefficient of viscosity (along the ordinate axis) of the ink liquid.

The point A represents the liquid which does not include the solute, that is, water. The coefficient of viscosity of water at 20° C. is about 1 (one) (more specifically, 1.0019), and the specific gravity of water at 20° C. is about 1 (one) (more accurately, 0.9982). The curve A-B-D represents the coefficient of viscosity of the ink liquid, and the curve A-C-D represents the specific gravity of the ink liquid, which vary depending on the variations of the weight percent of the solute included in the ink liquid.

A normal ink liquid includes a solute with a weight percent contained between the point $X_1$ and the point $X_2$. Thus, normal ink liquid has a coefficient of viscosity contained between the points $Y_1$ and $Y_2$. The above-mentioned normal ink liquid satisfies the various requirements which are already discussed. Now assume that the weight percent of the solute changes to the point $X_3$ due to the evaporation of the volatile component. The coefficient of the viscosity changes to the point $Y_3$ which is not suited for stable droplet formation. At this moment, the ink liquid has a specific gravity at the point $Z_3$. It will be clear from FIG. 1 that the specific gravity of the ink liquid must be maintained within the range between the points $Z_1$ and $Z_2$.

The present ink liquid viscosity control system is applicable to an ink liquid supply system, wherein the ink liquid temperature is held at a desired value, for example, 20° C. through the use of an ink liquid warmer system. A typical ink liquid warmer system is disclosed in U.S. Pat. No. 4,007,684, INK LIQUID WARMER FOR INK JET SYSTEM PRINTER, issued on Feb. 15, 1977.

Figure 2:
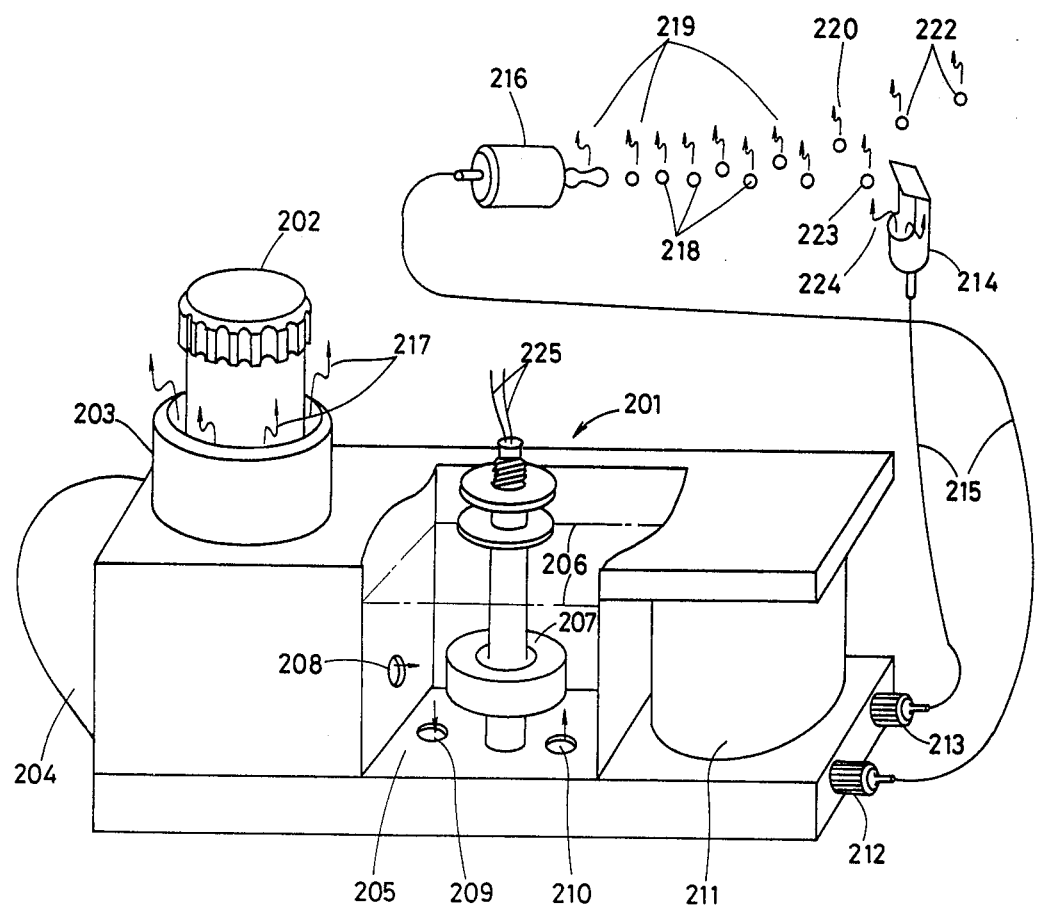
FIG. 2 is a schematic perspective view of an embodiment of an ink liquid supply system of the present invention.

FIG. 2 schematically shows an ink liquid supply system employing an embodiment of an ink liquid viscosity control system of the present invention. FIG. 2 is a partially cut away perspective view for clearly showing the location of the ink liquid viscosity detection unit. An ink liquid supply system 201 includes an ink cartridge 202 secured to a cartridge table 203. The ink liquid contained in the ink cartridge 202 is introduced into a sub tank 205 through an opening 208. The ink liquid contained in the sub tank 205 has a liquid level 206 which is identical with the liquid level of the ink liquid contained in the cartridge table 203. Another opening 209 is formed in the sub tank 205 for supplying the ink liquid contained in the sub tank 205 to a pump 204. The pump 204 develops an ink liquid under a predetermined pressure which is developed from the ink liquid supply system 201 through an outlet opening 212.

The thus developed ink liquid is supplied from the outlet opening 212 to an ink droplet issuance unit 216 through a flexible conduit 215. The ink droplet issuance unit 216 emits ink droplets 218 at a given frequency. Properly charged ink droplets 222 are directed to a recording paper by means of a pair of deflection plates, and ink droplets 223 not contributing to the actual printing operation are not charged and, hence, are directed to a beam gutter 214. The waste ink liquid collected by the beam gutter 214 is directed to an inlet opening 213 via a flexible conduit 215 for recirculation purposes. The inlet opening 213 is communicated with the pump 204. That is, the pump 204 functions not only to supply the ink liquid to the ink droplet issuance unit 216 but also to introduce the waste ink liquid collected at the beam gutter 214 into the ink liquid supply system 201. More specifically, the pump 204 includes a suction pump having an inlet communicated with the inlet opening 213 and an outlet thereof is communicated with an opening 210 formed in the sub tank 205. Thus, new ink liquid supplied from the cartridge table 203 is mixed with the old ink liquid supplied through the opening 210 in the sub tank 205. An electro-magnetic valve 211 is provided for selectively supplying the ink liquid to the ink droplet issuance unit 216.

A typical construction of the pump 204 for performing the above-mentioned operation is disclosed in co-pending U.S. patent application Ser. No. 070,639, now U.S. Pat. No. 4,278,984 for a CONSTANT FLOW RATE LIQUID SUPPLY PUMP, which was filed on Aug. 28, 1979 by Masafumi Matsumoto and Matahira Kotani, and assigned to the same assignee as the present applicaton. The German counterpart was laid open on Mar. 13, 1980 (DOS No. 2,934,947). Thus, the detailed construction of the pump 204 is omitted from the present specification for the purpose of simplicity.

As already discussed above, the solvent, water, volatilizes without regard to the operation of the ink jet system printer. More specifically, the cartridge table 203 and the sub tank 205 are communicated with an ambience air in order to maintain the ink liquid level 206 in the sub tank 205 at an identical level with that in the cartridge table 203. Thus, the solvent volatilizes as indicated by arrows 217 in FIG. 2. Further, during the operation of the ink jet system printer, the solvent volatilizes from the ink droplets 218 as indicated by arrows 219. The evaporation is at a considerably high level because the ink droplets 218 are very small, for example 100 $\mu\phi$. The evaporation of the ink droplets 222, which are directed to the recording paper, does not affect the print quality nor on the system operation. However, the evaporation of the ink droplets 223, which are directed to the beam gutter 214, affects the system operation because the ink liquid collected in the beam gutter 214 is returned to the ink liquid supply system 201. In addition, the solvent further volatilizes while the ink liquid is contained in the beam gutter 214 as indicated by arrows 224.

A float element 207 is disposed in the ink liquid contained in the sub tank 205. The float element 207 is constructed to show the specific gravity slightly greater than the preferred ink liquid, wherein the solvent has not volatilized. Therefore, the float element 207 is placed at the bottom of the sub tank 205 when the ink liquid has the preferred specific gravity, or the coefficient of the viscosity. When the solvent volatilizes, the coefficient of viscosity increases and the specific gravity of the ink liquid becomes greater than that of the float element 207. Then, the float element 207 moves upward. A guide member is disposed in the sub tank 205 for guiding the movement of the float element 207. A lead switch is disposed in the guide member for detecting the movement of the float element 207. More specifically, a ring magnet is installed in the float element 207 for switching the lead switch when the float element 207 travels upward. The detection signal derived from the lead switch is applied to a control unit via signal cables 225.

Figure 3:
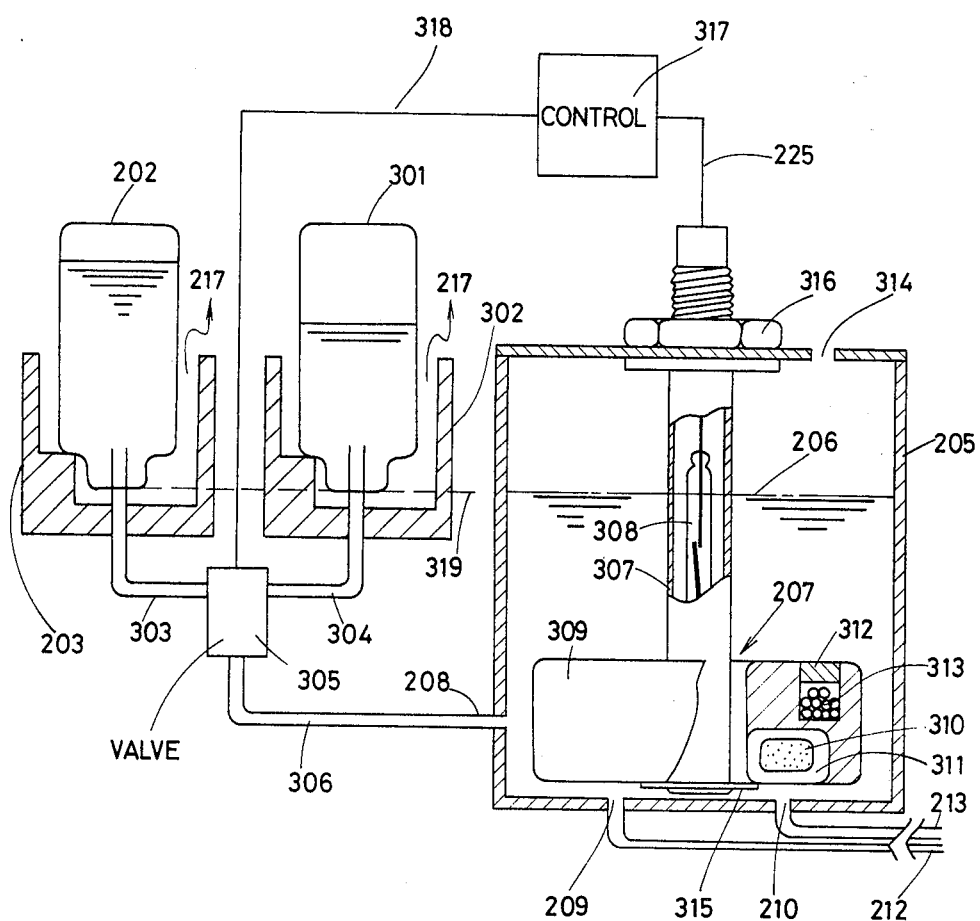
FIG. 3 is a sectional view of an embodiment of an ink liquid viscosity control system of the present invention.

FIG. 3 shows an embodiment of an ink liquid viscosity control system of the present invention. Like elements corresponding to those of FIG. 2 are indicated by like numerals.

The float element 207 comprises a float 309 of which the specific gravity is slightly (about 2/1000) greater than the maximum value (the point $Z_2$ in FIG. 1) of the specific gravity of the preferred ink liquid. The float 309 is made of polypropylene (the specific gravity is 0.90). A barium ferrite ring magnet 310 (the specific gravity is 4.6 through 4.9) is disposed in the float 309, and lead beads 313 are disposed in the float 309 for adjusting the total specific gravity of the float element 207. A polypropylene film 311 surrounds the ring magnet 310 for protection purposes, and a polypropylene cap 312 is provided for the lead beads container.

The float 309 is slidably secured to a stem 307. A lead switch 308 is disposed in the stem 307. The signal cables 225 of the lead switch 308 are connected to a control unit 317 for controlling an operation of an electro-magnetic cross valve 305. In the normal operation mode, the electro-magnetic cross valve 305 fuctions to communicate the ink cartridge 202 with the sub tank 205 through a conduit 303 and a conduit 306. As already discussed above, the liquid level 206 in the sub tank 205 is held identical with a liquid level 319 in the cartridge table 203.

A dilution cartridge 301 is provided for adding a dilution, namely, water to the ink liquid contained in the sub tank 205. In the normal operation mode, the float 309 is held at the bottom of the sub tank 205 to contact a stopper 315. The specific gravity of the ink liquid contained in the sub tank 205 gradually increases as already discussed above. When the specific gravity of the ink liquid in the sub tank 205 becomes greater than the specific gravity of the float element 207, the float element 207 begins to move upward along the stem 307. When the float element 207 reaches a portion where the lead switch 308 is located, the ring magnet 310 secured in the float element 207 functions to switch on the lead switch 308. The signal cables 225 transfer the detection output signal to the control unit 317, thereby energizing the electro-magnetic cross valve 305. Thus, a conduit 304, which is associated with the dilution cartridge 301, is communicated with the conduit 306. Accordingly, the ink liquid contained in the sub tank 205 is gradually diluted. When the specific gravity of the ink liquid in the sub tank 205 becomes smaller than that of the float element 207, the float element 207 travels downward to switch off the lead switch 308. Then, the electro-magnetic cross valve 305 is returned to the normal condition, wherein the conduit 303 is communicated with the conduit 306.

More specifically, if the specific gravity of the ink liquid in the sub tank 205 becomes $Z_3$ in FIG. 1, the float element 207 travels upward to switch on the lead switch 308, thereby diluting the ink liquid in the sub tank 205. Thus, the specific gravity of the ink liquid reduces toward the point $Z_2$ in FIG. 1. When the specific gravity of the ink liquid reaches the point $Z_2$, the dilution operation is terminated. Under these operations, the ink liquid viscosity is reduced from the point $Y_3$ to the point $Y_2$. That is, the coefficient of viscosity of the ink liquid is held below 2.8 cps (centipoise) which is below the required value 3.0 cps (centipoise).

The float element 207 comprises the polypropylene float 309 (volume $V_P$; density $\rho_P$), the barium ferrite ring magnet 310 (volume $V_M$; density $\rho_M$) and the gravity adjusting lead beads 313 (volume $V_L$; density $\rho_L$). Accordingly, the specific gravity D of the float element 207 is represented as follows:

$$D = \frac{V_P\rho_P + V_M\rho_M + V_L\rho_L}{V_W} \quad (1)$$

where: $V_W$ is the weight of the water of the same volume as the float element 207.

The lead bead 313 has a diameter of 1.5 millimeter. Therefore, one lead bead 313 has the weight:

$$\frac{4}{3}\pi r^3 \rho = \frac{4}{3}\pi(0.075)^3 \times 11.34 = 0.00176 \text{(grams)}$$

when n number of lead beads 313 are employed, the density $\rho_L$ can be represented as follows:

$$\rho_L = 0.00176 \times n/V_L$$

Accordingly, the equation (1) can be modified as follows:

$$D = \frac{V_P\rho_P + V_M\rho_M + 0.00176 \times n}{V_W} \quad (2)$$

The equation (2) is used to select the specific gravity of the float element 207 at the value 1.062 which is slightly greater than the maximum specific gravity of the preferred ink liquid.

When the float 309 is made of a polypropylene float having a size as shown below, the equation (2) is modified to a equation (3).

diameter: 14 millimeters
bore diameter: 7 millimeters
height: 13 millimeters $$1.062 = \frac{(1.154 \pm 5\%) \times 0.9 + (0.08 \pm 3\%) \times (4.6 \sim 4.9) + 0.0176 \times n}{2.000 \pm 5\%} \quad (3)$$

The equation (3) includes the working tolerance represented by the percent. If the float 309 is made at the maximum tolerance, the equation (3) is represented as follows:

$$\frac{0.0176 \times n}{1.9} = 1.062 - \frac{1.2117 \times 0.9 + 0.0824 \times 4.9}{1.9}$$

The desired beads number n is obtained from the above equation. That is, n=29.7 (approximately, 30).

On the other hand, if the float 309 is made as small as possible within the above tolerance, the desired beads number is obtained as follows:

$$\frac{0.0176 \times n}{2.1} 1.062 - \frac{1.0963 \times 0.9 + 0.0776 \times 4.6}{2.1}$$

n=50.37 (approximately, 50).

It will be clear from the foregoing description that a desired specific gravity can be applied to the float element 207 by adjusting the number of the lead beads 313. The lead beads 313 can be added or removed through an opening covered by the polypropylene cap 312.

Figure 4:
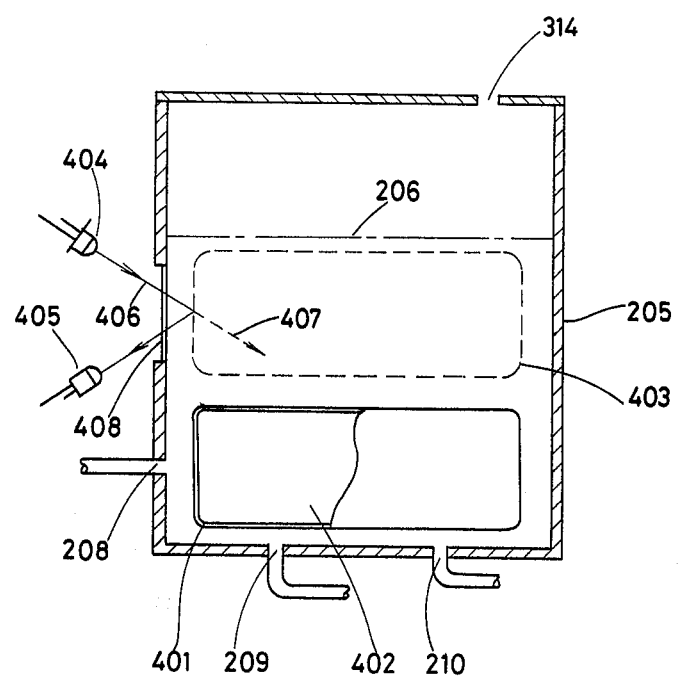
FIG. 4 is a sectional view of another embodiment of an ink liquid viscosity detection unit included in the ink liquid viscosity control system of the present invention.

FIG. 4 shows another embodiment of the ink liquid viscosity detection unit included in the ink liquid viscosity control system of the present invention. Like elements corresponding to those of FIG. 3 are indicated by like numerals.

A float 401 comprises a highly polymerised film such as a polyester film (specific gravity is 1.68). An ink liquid of the preferred specific gravity is disposed in the float 401. The preferred ink liquid is filled in the float 401 and, therefore, the float 401 is placed at the bottom of the sub tank 205 when the ink liquid in the sub tank 205 has the desired specific gravity. When the specific gravity of the ink liquid contained in the sub tank 205 increases, the float 401 moves upward as shown by broken lines 403. The sub tank 205 includes a transparent wall 408 through which a light beam 406 emitted from a light emitting diode 404 passes. Therefore, when the float 401 is located at the position shown by the broken lines 403, the reflected light reaches a light responsive element 405 such as a phototransistor. When the float 401 is located at the bottom of the sub tank 205, the light responsive element 405 does not receive the reflected light beam. A detection output signal of the light responsive element 405 is applied to the control unit 317 shown in FIG. 3, thereby controlling the operation of the electro-magnetic cross valve 305.

The invention being thus described, it will be obvious that the same may be varied in many ways. Such variations are not to be regarded as a departure from the spirit and scope of the invention, and all such modifications are intended to be included within the scope of the following claims.

What is claimed is:

1. An ink liquid viscosity control system in an ink liquid supply system for an ink jet system printer, said ink liquid supply system comprising an ink liquid reservoir for containing a new ink liquid therein, and a sub tank for containing a predetermined ink liquid supply having an ink liquid level and for introducing the new ink liquid from said ink liquid reservoir and developing the ink liquid to be supplied to an ink droplet issuance unit included in the ink jet system printer, said ink liquid viscosity control system comprising:

a float member being entirely submerged within the ink liquid contained in said sub tank, said float member having a specific gravity slightly greater than a specific gravity of a preferred ink liquid suited for the ink jet system printer;

detection means disposed below the ink liquid level for detecting a movement of said float member while said float member is entirely submerged within said sub tank and producing an output signal indicative thereof, said movement of said float member being caused by a variation in the specific gravity of the ink liquid contained in said sub tank; and viscosity adjusting means for maintaining the viscosity of the ink liquid contained in said sub tank within a preselected range in response to said output signal produced by said detection means;

said float member normally being entirely submerged, disposed in a lower portion of said sub tank and being unaffected by surface tension of the ink liquid level and being periodically, automatically moved upwardly, while still remaining entirely submerged within said ink liquid, in response to an increase in the specific gravity of said ink liquid above the specific gravity of said preferred ink liquid thereby actuating said detection means and producing said output signal for actuating said viscosity adjusting means for effecting a reduction in the viscosity of said ink liquid contained within said sub tank.

2. The ink liquid viscosity control system of claim 1, said viscosity adjusting means comprising a dilution tank for supplying a dilution to the ink liquid contained in said sub tank when said output signal is developed from said detection means.

3. The ink liquid viscosity control system of claim 2, said viscosity adjusting means further comprising:

an electro-magnetic cross valve;

a first conduit means disposed between said ink liquid reservoir and said electro-magnetic cross valve;

a second conduit means disposed between said dilution tank and said electro-magnetic cross valve; and a third conduit means disposed between said electro-magnetic cross valve and said sub tank, wherein said first conduit means is communicated with said third conduit means through said electro-magnetic cross valve in the normal operation mode, and said second conduit means is communicated with said third conduit means through said electro-magnetic cross valve when said output signal is developed from said detection means.

4. The ink liquid viscosity control system of claim 1, 2 or 3, said float member comprising:

a float body; and gravity adjusting means disposed in said float body for adjusting the specific gravity of the float member to said specific gravity slightly greater than the specific gravity of the preferred ink liquid suited for the ink jet system printer.

5. The ink liquid viscosity control system of claim 4, said float member further comprising a magnet disposed in said float body, and wherein said detection means comprises a lead switch secured at a desired portion in said sub tank, said lead switch being associated with said magnet so that said lead switch is switched when said magnet disposed in said float body moves upward in unison with said movement of said float member within said sub tank.

6. The ink liquid viscosity control system according to claim 2, wherein said float normally results in a closure of a supply conduit from said dilution tank when said float is in the lower position and as said float periodically moves upwardly in response to changes in the specific gravity of said ink liquid said supply conduit is opened to supply a dilution to said ink liquid to lower the viscosity of said ink liquid.

7. The ink liquid viscosity control system according to claim 1, wherein said sub tank includes a transparent wall section and said detection means includes a light emitting diode and a light responsive element operatively positioned adjacent to said transparent wall section of said sub tank, whereby light is reflected off of said float to actuate said light responsive element and said viscosity adjusting means when said float moves upwardly to be adjacent to said transparent wall section in response to an increase in the viscosity of the ink liquid within said sub tank.

8. The ink liquid viscosity control system according to claim 1, and further including a beam gutter means for recirculating unused ink droplets back to said sub tank.

* * * * *